United States Patent [19]

West et al.

[11] Patent Number: 4,862,904
[45] Date of Patent: Sep. 5, 1989

[54] I. V. STABILIZER

[76] Inventors: Jane E. West; Thomas C. West, both of 2720 Kimberlea, Muskogee, Okla. 74403

[21] Appl. No.: 130,476

[22] Filed: Dec. 8, 1987

[51] Int. Cl.⁴ .............................................. A61F 13/00
[52] U.S. Cl. ..................................................... 128/877
[58] Field of Search ........ 128/133, DIG. 6, DIG. 10, 128/DIG. 15, DIG. 26, 135, 87 R; 604/178–180

[56] References Cited

U.S. PATENT DOCUMENTS

| | | | |
|---|---|---|---|
| 3,888,244 | 6/1975 | Lebold | 128/165 |
| 3,933,150 | 1/1976 | Kaplan et al. | 128/24 R |
| 4,043,330 | 8/1977 | Bansal | 128/133 |
| 4,156,425 | 5/1979 | Arkans | 128/24 R |
| 4,183,098 | 1/1980 | Knowles, Jr. | 128/87 R |
| 4,215,687 | 8/1980 | Shaw | 128/169 |
| 4,286,588 | 9/1981 | Lovegrove | 128/133 |
| 4,316,461 | 2/1982 | Marais et al. | 128/133 |
| 4,436,088 | 3/1984 | Finnieston | 128/133 |
| 4,449,975 | 5/1984 | Perry | 128/133 |
| 4,470,410 | 9/1984 | Elliott | 128/133 |
| 4,481,942 | 11/1984 | Duncan | 128/133 |
| 4,531,942 | 7/1985 | Turner | 128/DIG. 26 |
| 4,569,348 | 2/1986 | Hasslinger | 604/179 |
| 4,584,993 | 4/1986 | Nelson | 128/87 R |
| 4,587,962 | 5/1986 | Greene et al. | 128/80 H |
| 4,671,787 | 6/1987 | Widman | 128/DIG. 26 |

Primary Examiner—Robert A. Hafer
Assistant Examiner—Charles H. Sam

[57] ABSTRACT

An I. V. stabilizer has an elongated rectangular arm support pad onto which eight hook and loop fastener straps are secured. The straps are spaced along the length of the pad in four sets of two. Each set of the four straps and the arm support pad has an inner lining of padded foam material and a sterile cotton backing. The arm support pad as a central enclosed plastic stiffener which extends along the length of the pad. In use, a person's arm is placed on the support pad and the I. V. needle is then inserted. The four inner straps are wrapped around the person's arm and supported by cooperating hook and loop fasteners on the cotton backing of the support pad. The I. V. tube is then looped over the inner straps and the outer straps are then wrapped over the I. V. tube, and around the individual's arm and secured by hook and loop fasteners on the cotton backing of the support pad. In this manner, a secure support of an I. V. needle and tube is provided, preventing the I. V. from being dislodged from the individual's arm.

2 Claims, 3 Drawing Sheets

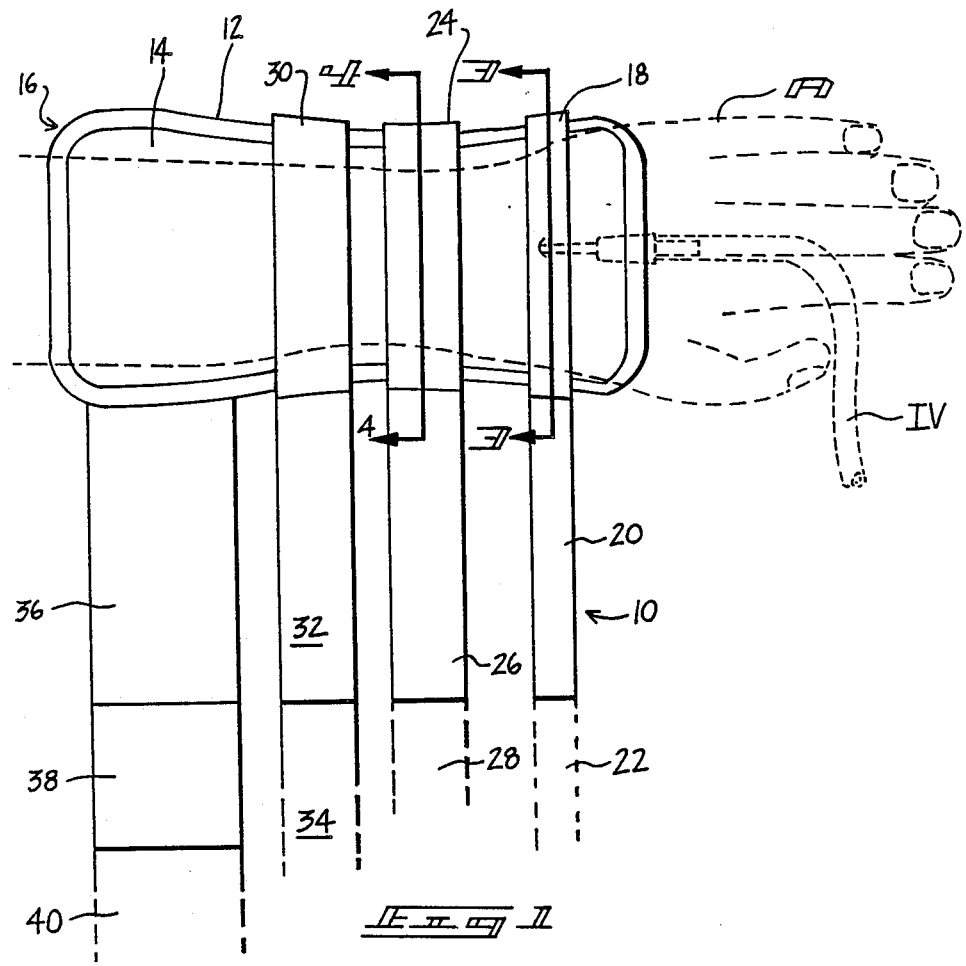
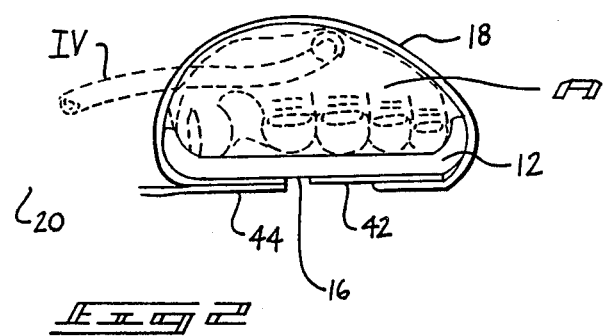

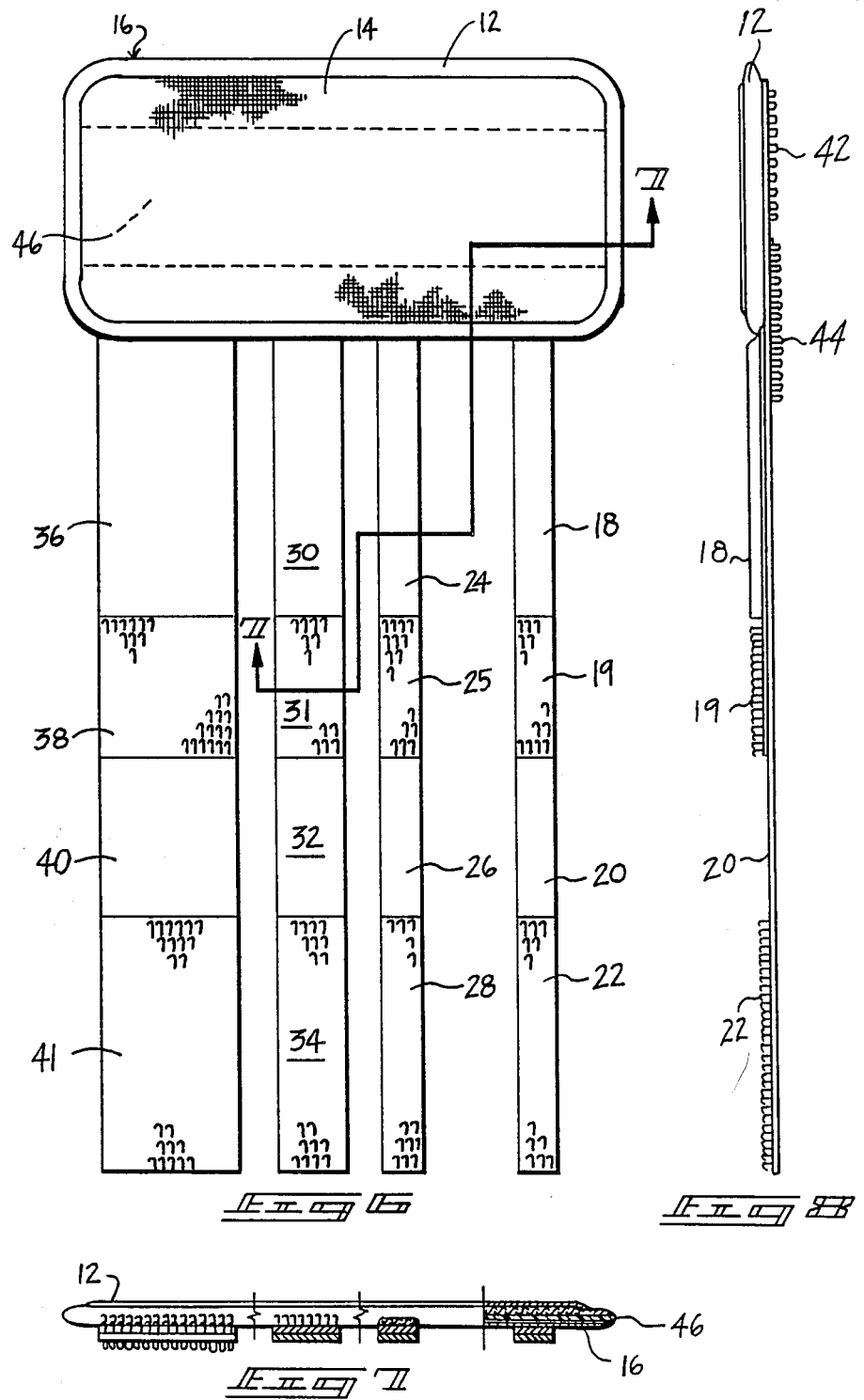

I. V. STABILIZER

BACKGROUND OF THE INVENTION

1. Field of the Invention

The present invention relates to I.V. stabilizers, and more particularly pertains to a new and improved I.V. stabilizer for maintaining an I.V. needle and tube secured to the arm of an individual. Currently, tape is often used to maintain I.V. needles and tubes secured in position on an individual's arm. The use of tape has several disadvantages, especially if used over a prolonged period of time. These disadvantages include the painful removal of the tape from the individual's arm as well as possible allergies and skin irritation due to long term exposure to the adhesive tape. Also, tape alone does not provide an adequate support to maintain an I.V. tube and needle secured in the proper position. In order to overcome these disadvantages, the present invention provides an I.V. stabilizer with a padded arm support and hook and loop fastener straps to properly maintain an I.V. needle and tube in position on a patient's arm.

2. Description of the Prior Art

Various types of support devices adapted to be secured around limbs of an individual are known in the prior art. A typical example of such a support device is to be found in U.S. Pat. No. 3,933,150, which issued to B. Kaplan et al on Jan. 20, 1976. This patent discloses a gas pressurizable support adapted to be secured around a patient's legs and inflated to treat shock victims by reducing the volume of blood pooled in the legs and abdomen of the patient. This device utilizes a plurality of spaced hook and loop fastening straps. U.S. Pat. No. 4,156,425, which issued to E. Arkans on May 29, 1979, discloses a support sleeve adapted to be wrapped around a patient's leg and pressurized by an external source of pressurized fluid. The device utilizes a spaced series of hook and loop securing straps. U.S. Pat. No. 4,215,687, which issued to F. Shaw on Aug. 5, 1980, discloses a limb encircling therapeutic device which utilizes a series of spaced VELCRO fastening straps to secure the device around the limb of a patient. U.S. Pat. No. 4,569,348, which issued to R. Hasslinger on Feb. 11, 1986, discloses a catheter tube holder strap which is adapted to be secured by a hook and loop fastening strap around the leg of a patient. A bushing is provided for the reception of a catheter tube U.S. Pat. No. 4,587,962, which issued to T. Greene et al on May 13, 1986, discloses a leg supporting jacket for supporting the injured leg of a patient. A spaced series of hook and loop fastening straps are utilized to tension the jacket around the leg of the patient.

While the above mentioned devices are suited for their intended usage, none of these devices provide an I.V. stabilizer which utilizes a padded arm support with a series of overlying hook and loop fastened securing straps. Additionally, none of the aforesaid prior art devices contemplates the provision of an I. V. stabilizer with an arm support pad with an embedded stiffening slat and a series of pairs of spaced overlying hook and loop fastening straps. Inasmuch as the art is relatively crowded with respect to these various types of support devices, it can be appreciated that there is a continuing need for and interest in improvements to I.V. stabilizers, and in this respect, the present invention addresses this need and interest.

SUMMARY OF THE INVENTION

In view of the foregoing disadvantages inherent in the known types of I.V. securing devices now present in the prior art, the present invention provides an improved I.V. stabilizer. As such, the general purpose of the present invention, which will be described subsequently in greater detail, is to provide a new and improved I.V. stabilizer which has all the advantages of the prior art I.V. securing devices and none of the disadvantages.

To attain this, a representative embodiments of the concepts of the present invention is illustrated in the drawings and make use of an I.V. stabilizer which has an elongated rectangular arm support pad onto which eight hook and loop fastener straps are secured. The straps are spaced along the length of the pad in four sets of two. Each set of two straps consists of overlying inner and outer straps. Each of the four inner straps and the arm support pad has an inner lining of padded foam material and a sterile cotton backing. The arm support pad has a central enclosed plastic stiffener which extends along the length of the pad. In use, a person's arm is placed on the support pad and the I.V. needle is then inserted. The four inner straps are wrapped around the person's arm and secured by cooperating hook and loop fasteners provided on the cotton backing of the support pad. The I.V. tube is then looped over the inner straps and the outer straps are then wrapped over the I.V. tube, around the individual's arm and secured by hook and loop fasteners on the cotton backing of the support pad. In this manner, a secure support of an I.V. needle and tube is provided, preventing the I.V. from being dislodged from the individual's arm.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved I.V. stabilizer which has all the advantages of the prior art I.V. securing devices and none of the disadvantages.

It is another object of the present invention to provide a new and improved I.V. stabilizer which may be easily and efficiently manufactured and marketed.

It is a further object of the present invention to provide a new and improved I.V. stabilizer which is of a durable and reliable construction.

An even further object of the present invention is to provide a new and improved I.V. stabilizer which is susceptible of a low cost of manufacture with regard to both materials and labor, and which accordingly is then susceptible of low prices of sale to the consuming public, thereby making such I.V. stabilizers economically available to the buying public.

Still yet another object of the present invention is to provide a new and improved I.V. stabilizer which provides in the apparatuses and methods of the prior art some of the advantages thereof, while simultaneously overcoming some of the disadvantages normally associated therewith.

Still another object of the present invention is to provide a new and improved I.V. stabilizer which utilizes a padded arm support with an enclosed stiffening slat.

Yet another object of the present invention is to provide a new and improved I.V. stabilizer for maintaining an I.V. needle and tube secured in a proper position on a patient's arm without utilizing adhesive tape.

Even still another object of the present invention is to provide a new and improved I.V. stabilizer which utilizes a stiffened padded arm support pad with a series of spaced pairs of overlying hook and loop fasten straps to secure an I.V. needle and tube to the arm of a patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top view of the I.V. stabilizer of the present invention, in the process of being secured to the arm of a patient.

FIG. 2 is an end view of the I.V. stabilizer of FIG. 1.

FIG. 6 is a top view of the I.V. stabilizer of the present invention, with all of the fastening straps stretched out adjacent the arm support pad.

FIG. 7 is a cross sectional view taken along 7—7 of FIG. 6, illustrating the internal construction of the I.V. stabilizer of the present invention.

FIG. 8 is an end view of the I.V. stabilizer device of FIG. 6.

DESCRIPTION OF THE PREFERRED EMBODIMENT

Figure 3:
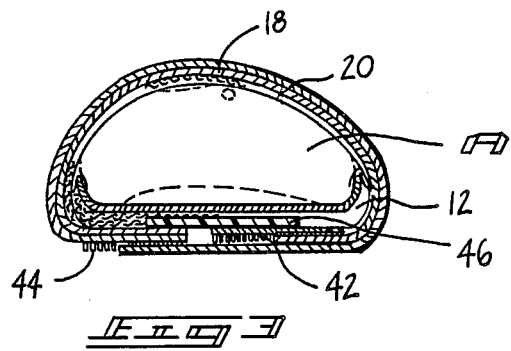
FIG. 3 is a transverse cross sectional view taken along line 3—3 of FIG. 1, illustrating the I.V. stabilizer of the present invention.

With reference now to the drawings, and in particular to FIG. 1 thereof, a new and improved I.V. stabilizer embodying the principles and concepts of the present invention and generally designated by the reference numeral 10 will be described.

More specifically, it will be noted that the first embodiment 10 of the invention includes an arm support pad 12 having a first side 14 lined with a padded foam material. The opposite side 16 of the arm support pad 12 is covered with a sterile cotton backing material which is folded over the edges of the foam material and stitched thereto. Four pairs of overlying fastening straps are spaced along the length of the arm support pad 12. A first pair of fastening straps includes an inner strap 18 and an outer strap 20. A second pair of overlying fastening straps includes an inner fastening strap 24 and an outer fastening strap 26. A third pair of overlying fastening straps includes an inner fastening strap 30 and an outer fastening strap 32. A fourth pair of overlying fastening straps includes an inner fastening strap 36 and an outer fastening strap 40. Each of the inner fastening straps 18, 24, 30 and 36 are formed from a padded foam lining material provided with a sterile cotton backing. Each of the fastening straps are provided with an end portion having a hook and loop fastening strip 22, 28, 34, and 38. Hook and loop fasteners sold under the trademark VELCRO are representative of the fasteners which may be used. In use, a patient's arm A is placed on the arm support pad 12 and the I.V. needle is inserted into the patient's arm. At this point, the inner fastening strap 18 is wrapped around the wrist of the patient's arm, over the I.V. tube. The three remaining padded inner fastening straps 24, 30 and 36 are then wrapped around the patient's arm and fastened to cooperating hook and loop fasteners on the cotton backing 16 of the arm support pad 12. The I.V. tube is then looped over the top surface of the inner fastening straps 18, 24, 30 and 36 and secured by wrapping the outer fastening straps 20, 26, 32, and 40 over the I.V. tube, around the patient's arm and securing the outer fastening straps on cooperating hook and loop fasteners on the cotton backing material 16 of the arm support pad 12. In this manner, the I.V. tube will be secured between the inner and outer fastening strap, thus preventing the I.V. needle from becoming dislodged from the patient's arm A and also preventing the I.V. tube from uncomfortably pressing against the patient's skin.

In FIG. 2, an end view of the I.V. stabilizer 10 of the present invention is provided, illustrating the end most inner fastening strap 18 wrapped around the patient's arm A and secured to a hook and loop fastening strip 42 on the cotton backing material 16 of the arm support pad 12. A second hook and loop fastening strip 44 is provided on the underside of each of the outer fastening straps.

In FIG. 3, the outer fastening strap 20 is shown wrapped around the patient's arm A and secured by the fastening strip 44. An elongated stiffening slat 46 extends centrally along the length of the arm support pad 12, and is enclosed between the padded foam material and the cotton backing material. The stiffening slat 46 is preferably formed from a plastic material with sufficient rigidity to provide adequate stiffness to the arm support pad 12.

Figure 4:
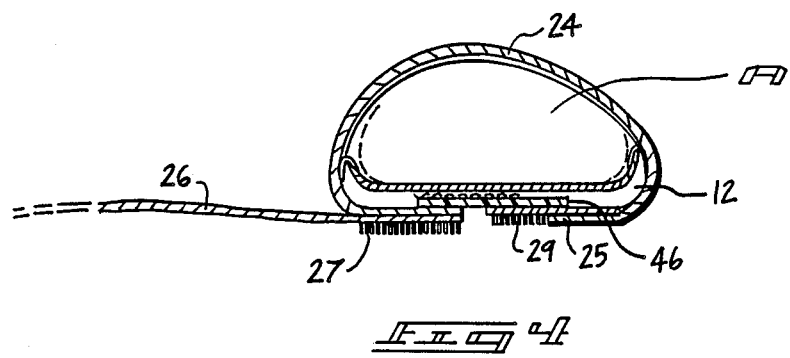
FIG. 4 is a transverse cross sectional view taken along line 4—4 of FIG. 1, illustrating the I.V. stabilizer of the present invention.

In the cross sectional view of FIG. 4, the inner fastening strap 24 of the second pair of overlying fastening straps is illustrated wrapped around the patient's arm A, with a hook and loop fastening portion 25 on the end of the strap 24 in engagement with a cooperating hook and loop fastening strip 29 on the cotton backing material 16. A second hook and loop fastening strip is provided on the underside of the outer fastening strap 26. The outer fastening strap 26, in use, is wrapped over the I.V. tube, around the patient's arm, and secured to the hook and loop fastening strip 27, in a fashion analogous to that illustrated in FIG. 3.

Figure 5:
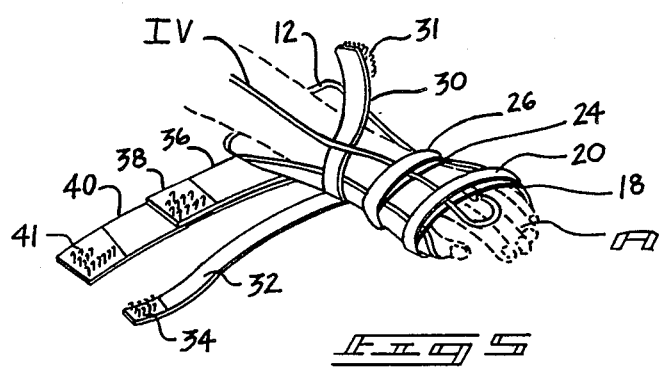
FIG. 5 is a perspective view of the I.V. stabilizer of the present invention, in the process of being secured to the arm of a patient.

In the perspective view of FIG. 5, the I.V. stabilizer 10 of the present invention is illustrated in the process of being secured to a patient's arm A. The I.V. tube will be sandwiched between the inner fastening straps and the outer fastening straps. The third pair of overlying fastening straps includes an inner fastening strap 30 having hook and loop fastening strip 31 and an outer fastening strap 32 having a hook and loop fastening strip 34. The fourth pair of overlying fastening straps includes an inner fastening strap 36 having a hook and loop fastening strip 38 and an outer fastening strap 40 having a hook and loop fastening strip 41.

In the top view of FIG. 6, the arm support pad 12 is illustrated with the four overlying pairs of fastening straps stretched out laterally from the side edge of the arm support pad 12. Each of the four pairs of fastening straps are stitched in the illustrated overlying relation along the side edge of the arm support pad 12. It is contemplated that the first pair of overlying fastening straps 18 and 20 and the second pair of overlying fastening straps 24 and 26 will have a width of approximately one half inch. The width of the third pair of overlying fastening straps 30 and 32 will be approximately one inch and the width of the fourth pair of overlying fastening straps 36 and 40 will be approximately two inches. These dimensions have been carefully selected to provide adequate support to the I.V. needle and tube, while providing sufficient access to the needle and tube and allowing air circulation to the patient's arm. The arm support pad 12 is formed in a generally rectangular shape, having a width of approximately four inches and a length of approximately eight inches. The elongated stiffening slat 46 is enclosed centrally within the arm support pad 12, and has an approximately two inch width. It is pointed out that each of the outer fastening straps 20, 26, 32 and 40 are provided with end portions having hook and loop fastening strips 22, 28, 34 and 41. It should also be noted that each of the outer fastening straps 20, 26, 32 and 40 are longer than the inner fastening straps 18, 24, 30 and 36. This extra length allows easy access to the ends of the inner fastening straps and allows a sufficient range of adjustability for the outer fastening straps.

The cross sectional view of FIG. 7 illustrates the overlying relation of the fastening straps and the enclosed elongated stiffening slat 46.

By reference to FIG. 8, the relative thickness of the various elements of the present invention may be understood. It is again pointed out that each of the inner fastening straps are provided with a foam lining material and a sterile cotton backing material. The foam lining material on each of the inner fastening straps 18, 24, 30 and 36 provides an enhanced degree of comfort to the patient.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An I.V. stabilizer, comprising:
    a generally rectangular elongated arm support pad dimensioned for extent along a substantial portion of an individuals forearm;
    said pad having a first side lined with a padded foam material and second side covered with a sterile cotton backing material;
    a narrow elongated stiffening slat extending centrally along the length of said pad and having a width less than said pad;
    said slat enclosed between said foam lining material and said cotton backing material;
    four pairs of elongated overlying fastening straps attached to a side edge of said support pad in parallel spaced relation along the length of said arm support pad;
    hook and loop fastening means on said cotton backing material of said pad;
    cooperating hook and loop fastening means on end portions of each of said fastening straps;
    an inner one of each of said pairs of overlying fastening straps being shorter than an outer one of each of said pairs of fastening strips; and
    said inner one of each of said pairs of overlying fastening straps having a foam material lining and a sterile cotton backing.

2. The I.V. stabilizer of claim 1, wherein a first pair of overlying fastening straps have a width of approximately two inches, a second pair of overlying fastening straps have a width of approximately one inch, and two of said pairs of overlying fastening straps have a width of approximately one half inch.

* * * * *